US005977086A

United States Patent [19]
Lisziewicz et al.

[11] Patent Number: 5,977,086
[45] Date of Patent: Nov. 2, 1999

[54] METHOD OF INHIBITING HUMAN IMMUNODEFICIENCY VIRUS BY COMBINED USE OF HYDROXYUREA, A NUCLEOSIDE ANALOG, AND A PROTEASE INHIBITOR

[75] Inventors: Julianna Lisziewicz; Franco Lori, both of Bethesda, Md.

[73] Assignee: R.I.G.H.T., Washington, D.C.

[21] Appl. No.: 09/056,691

[22] Filed: Apr. 8, 1998

Related U.S. Application Data

[63] Continuation of application No. 08/812,515, Mar. 7, 1997.
[51] Int. Cl.$^6$ .......................... A61K 31/70; A61K 31/17
[52] U.S. Cl. ............................ 514/45; 514/588; 514/441
[58] Field of Search ............................... 514/50, 588, 45, 514/441

[56] References Cited

U.S. PATENT DOCUMENTS

| 5,026,687 | 6/1991 | Yarchoan et al. . |
| 5,110,600 | 5/1992 | Green . |
| 5,250,563 | 10/1993 | Chen et al. ............................. 514/411 |
| 5,300,059 | 4/1994 | Rubinstein et al. . |

FOREIGN PATENT DOCUMENTS

| 94918016 | 5/1994 | European Pat. Off. . |

OTHER PUBLICATIONS

Fundamental Virology, Second Ed., Ch. 27 edited by Fields, et al. Raven Press Ltd., NY, NY 1991.
Borrow et al.; Nature Medicine, 3:(2) 205–211, 1997.
Goulder et al.; Nature Medicine, 3:(2) 212–217,,1997.
Mellors et al.; 272(5265) 1167–1170, May 1996.
Antiviral Therapy for Human Immunodefiency Virus Infections, E. De Clercq, Clinicial Microbiology Reviews 8:2, American Society for Microbiology (Apr. 1995).
Hydroxyurea as an Inhibitor of Human Immunodeficiency Virus–Type 1 Replication, F. Lori et al; Science 266: 801–805 (1994).
Hydroxyurea and AIDS: An Old Drug Finds a New Application? F. Lori et al. Aids Research and Human Retroviruses vol. 11, No. 10 Mary Ann Liebert, Inc. (1995).
Gao et al., Journal of Biological Chemistry, Apr. 29, 1994, 269(17); 12633–8. Divergent Anti–human Immunodefiency Virust Activity and Anabolic Phosphorylation . . . .
Gao et al., Journal of Clinical Investigation, May 10, 1993; 91(5):2326–33, Differential Phosphorylation of Azidothymidine, Dideoxycyctidine, and Dideoxyinosine in Resting and Activated Pheripheral Blood.
Zhu et al.; Science, vol. 261 (5125); 1179–81; Genotypic and Phenotypic Characterization of HIV–1 in Patients with Primary Infection, 1993.
van't Wout et al.; Journal of Clinical Investigation, Nov. 1994: 94(5): 2060–7. Macrophage–tropic Variants Initiate Human Immunodefiency Virus Type 1 Infection after Sexual, Parenteral, and Vertical Transmission.

Reinhardt et al.; Journal of Clinical Microbiology, Feb. 1995; 33(2), 292–7, Human Cord Blood Mononuclear Cells are Preferentially Infected by Non–Syncytium–Inducing, Macrophage–Tropic . . . .
Ometto et al.; AIDS, 1995 May 9(5); 427–34: Viral photype and host–cell susceptibility to HIV–1 infection as risk factors for mother–to–child HIV–1 transmission.
Cameron et al.; Journal of Experimental Medicine, Apr. 1, 1996; 183(4); 1851–6: The Interaction of Macrophage and Non–Macrophage Tropic Isolates of HIV–1 with Thymic and Tonsillar Dendritic.
Seminars in Oncology; R. C. Donehower, 19:3 (Suppl. 9), 11–19 (1992); Current Advances in Hydroxyurea Ther.
Zack et al.; Cell 61:213 (1990) HIV–1 Entry into Quiescent Primary Lymphocytes: Molecular Analysis Reveals a Labile, Latent Viral Structure.
Zack et al.; Journal of Virology; 66:1717 (1992); Incompletely Reverse–Transcribed Human Immunodefiency Virus Type 1 Genomes in Quiescent Cells can Function as Intermediates . . . .
Stevenson et al.; EMBO J. 9:1551 (1990); HIV–1 Replication is controlled at the level of T Cell Activation and Proviral Integration.
Burinsky et al.; Science 254:423 (1991); Quiescent T Lymphocytes as an Inducible Virus Reservoir in HIV–1 Infection.
Lori et al.; Journal of Virology, 66:5067 (1992); Viral DNA Carried by Human Immunodeficiency Virus Type 1 Virions.
Pantaleo et al; Nature, 362(6418): 355–358 (1993); HIV Infection is Active and Progressive in Lymphoid Tissue During the Clinically Latent Stage of Disease.
Fox et al.; In Situ Hybridization for Detection of HIV RNA in Cells and Tissues; Current Protocols in Immunology, vol. 3 (Coligan et al. eds.) Wiley, NY, 1993.
Fox et al.; Microscopy Research and Technique; 25:78–84, 1993; In Situ Hybridization in HIV Research.
Methods in Molecular Biology, vol. 15: PCR Protocols; Humana Press, Inc. (1993).
Xiping et al.; Nature 1995; 373:117–122; Viral Dynamics in Human Immunodeficiency Virus Type 1 Infection.
Saag et al.; The New England Journal of Medicine; 1993; 329:1065–72; A short–Term Clinical Evaluation of . . . .
Boom et al.; Journal of Clinical Microbiology; 28:495–503 (1990); A Rapid and Simple Method for Purification of Nucleic Acids.
van Gemen et al.; Journal of Virological Methods; 43:177–188(1993); Quantitation of HIV–1 RNA in Plasma.

(List continued on next page.)

*Primary Examiner*—Gary L. Kunz
*Attorney, Agent, or Firm*—Valerie E. Looper

[57] ABSTRACT

A method for inhibiting replication of reverse transcriptase dependent virus in plant or animal cells, comprising the step of administering to said cells a combination of compounds selected from the group consisting of hydroxyurea, a nucleoside analog, and a protease inhibitor.

7 Claims, 3 Drawing Sheets

OTHER PUBLICATIONS

Kievits et al.; Journal of Virological Methods 35:3 273–286(1991); NASBA isothermal enzymatic in vitro nucleic acid amplification optimized for the diagnosis of HIV–1 infection.

van Gemen et al.; Journal of Virological Methods; (1994) 49: 157–168; A One–Tube Quantitative HIV–1 RNA NASBA nucleic acid amplification assay using electro-chemiluminescent (ECL) labeled probes.

Katzenstein et al.; The New England Journal of Medicine; Oct. 1996. 10:335(15): 1091–8; The Relation of Virologic and Immunologic Markers to Clinical Outcomes after Nucleoside Therapy in . . . .

SH
[DFTx]

-13

Start Therapy

5

33

50

119

167

Controls

Negative

Positive

Controls

Negative

Positive

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human immunodeficiency virus type 1

(xi) SEQUENCE DESCRIPTION: SEQ ID NO: 1:

GGACCTACAC CTGTCAACAT                                              20

(2) INFORMATION FOR SEQ ID NO: 2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Human immunodeficiency virus type 1

(viii) POSITION IN GENOME:
        (B) MAP POSITION: 886 to 908 of HXB2 pol gene
        (C) UNITS: bp (xi) SEQUENCE DESCRIPTION: SEQ ID NO: 2:

CATTTATCAG GATGGAGTTC ATA                                          23

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

GGATGGAAAG GATCACCAGC                                              20

(2) INFORMATION FOR SEQ ID NO: 4:

(i) SEQUENCE CHARACTERISTICS:
        (A) LENGTH: 22 base pairs
        (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
         (A) ORGANISM: Human immunodeficiency virus type 1

(xi) SEQUENCE DESCRIPTION: SEQ ID NO: 4:

TACTAGGTAT GGTAAATGCA GT                                                    22

(2) INFORMATION FOR SEQ ID NO: 5:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Human immunodeficiency virus type 1

(viii) POSITION IN GENOME:
         (B) MAP POSITION: 233 to 254 of HXB2 pol gene
         (C) UNITS: bp (xi) SEQUENCE DESCRIPTION: SEQ ID NO: 5:

CAGGAATGGA TGGCCCAAAA GT                                                    22

(2) INFORMATION FOR SEQ ID NO: 6:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: YES (vi) ORIGINAL SOURCE:
         (A) ORGANISM: Human immunodeficiency virus type 1

(viii) POSITION IN GENOME:
         (B) MAP POSITION: 874 to 891 of HXB2 pol gene
         (C) UNITS: bp (xi) SEQUENCE DESCRIPTION: SEQ ID NO: 6:

TTCATAACCC ATCCAAAG                                                         18
```

METHOD OF INHIBITING HUMAN IMMUNODEFICIENCY VIRUS BY COMBINED USE OF HYDROXYUREA, A NUCLEOSIDE ANALOG, AND A PROTEASE INHIBITOR

This is a continuation of U.S. Ser. No. 08/812,515 filed Mar. 7, 1997.

FIELD OF THE INVENTION

The present invention relates generally to the field of treatment human beings with Human Immunodeficiency Virus (HIV) infections. The inventors have found that the combination of hydroxyurea (HU), a nucleoside analog, and a protease inhibitor is capable of reducing the presence of the virus in both plasma and lymph nodes. Further, an individual has been shown to have no sign of viral rebound in plasma after discontinuing treatment for at least five weeks.

BACKGROUND OF THE INVENTION

Viruses are microorganisms that depend, to some degree, on host cell components for their growth and replication. Viral infection and replication in host cells generally results in disease, whether the host is an animal or plant. Human diseases caused by viral infections include the acquired immunodeficiency syndrome (AIDS) and hepatitis. A general discussion of this field is presented in *Fundamental Virology, Second Edition*, (ed. B. N. Fields, D. M. Knipe, R. M. Chanock, M. S. Hirsh, J. L. Melnick, T. P. Monath, and B. Roizman, Raven Press, Ltd., New York, N.Y. 1991).

Retrovirus Replication

Retroviruses comprise a large family of viruses that primarily infect vertebrates. Many diseases, including the induction of some tumors, are associated with retroviral infection (see *Fundamental Virology*, supra, pp. 645–708). All retroviruses, regardless of their clinical manifestations, have related structures and modes of replication.

Retroviruses contain an RNA genome that is replicated through a DNA intermediate. Inside the cell, the viral genome serves as a template for the synthesis of a double-stranded deoxyribonucleic acid (DNA) molecule that subsequently integrates into the genome of the host cell. This integration occasionally results in the induction of a tumor in the infected host organism. Following integration, a complex sequence of events leads to the production of progeny virions which are released from the infected cell.

Early in the retroviral life cycle, the RNA genome is copied into DNA by the virally encoded reverse transcriptase (RT). This enzyme can use both RNA and DNA templates, thereby producing the first strand of DNA (the negative strand) from the infecting RNA genome and a complementary second strand (the positive strand) of DNA using the first DNA strand as a template. To synthesize these DNA strands, the RT utilizes cellular substrates called deoxynucleoside triphosphates (dNTP).

Human retroviruses can be grouped into the leukemia viruses (HTLV type viruses) and the immunodeficiency viruses (HIV type viruses). HTLV infection may lead to one form of leukemia. Acquired immunodeficiency syndrome (AIDS) is caused by a form of HIV, with HIV-1 being more virulent than HIV-2. Both HTLV and HIV infect peripheral blood lymphocytes (PBL).

HIV Infection

HIV-1 was first identified as the causative agent of AIDS in 1983. The AIDS pandemic is now one of the most serious health problems worldwide. Catastrophic medical and social consequences are likely to extend into the next century. The World Health Organization (WHO) has estimated that between eight and ten million people are currently infected with HIV, and that approximately ten times as many individuals will be affected in the next decade. The large pool of HIV carriers makes the development of effective antiviral treatments a medical priority.

The initial HIV-1 infection may occur without accompanying symptoms, but most of the patients experience an acute HIV syndrome within 2 to 6 weeks of exposure to the virus. This syndrome is characterized by fever, headaches, sore throat with pharyngitis, generalized lymphadenopathy and rashes. During this phase the virus is replicating abundantly and is detectable in the blood and the CD4+T-cell number falls from a normal amount of $1000/mm^3$ to about $500/mm^3$. Antibdies to HIV-1 proteins appear in the serum between 2–12 weeks after primary infection. The sequence of appearance of these antibodies can be followed by the Western blot test, which detects the serum antibodies that bind to specific viral proteins. A positive Western blot response to gp160, gp120, p65, p55, gp41, p32, p24 and p18 proteins demonstrates that antibodies to various HIV-1 proteins are being produced. The process of change from negative for all the proteins to positive for the entire set is referred to as seroconversion. It has recently been demonstrated that during seroconversion there is a high level of virus present in the blood. The cellular arm of the immune response is also activated during seroconversion. (Borrow et al. Nature Medicine 3:(2) 212–217, 1997; Goulder et al. Nature Medicine 3:(2) 205–211, 1997). Both humoral and cellular immune response together are associated with the decline of viral load in body fluids, or viremia, during acute primary infection. In the absence of antiviral therapy, the immune system can partially control viremia. When the viremia decreases in the blood, the CD4+T-cell number rises, but absent effective treatment, the T-cell population never fully recovers to the normal level.

Viral load, measured as HIV-1 RNA is the best available indicator of disease progression and reduced concentration of HIV-1 in various tissues and fluids in response to anti-retroviral therapy is predictive of improved prognosis (Mellors, J. W. et al. Science 272(5265) 1167–1170, 1996).

Antiviral Therapies

There is a critical need to develop effective drug treatments to combat RT-dependent viruses such as HIV. Such efforts were recently urged in the United Kingdom-Irish-French Concorde Trial conclusions which reported that the nucleoside analog zidovudine (AZT), a mainstay in the treatment of patients infected with HIV-1, failed to improve the survival or disease progression in asymptomatic patients. Other nucleoside analogs such as 2',3'-dideoxyinosine (ddI) are currently under evaluation. The effects of ddI on disease progression and patient survival endpoints have not been adequately investigated. Non-competitive HIV-1 RT inhibitors and HIV-1 protease inhibitors have also been recently developed. These materials have different antiviral activities and pharmacokinetics properties, but they all directly target HIV-1 proteins. Despite the high efficacy of these compounds, the initial in vitrolin vivo testing has been characterized by the rapid onset of variants of HIV-1 resistant to these drugs. These drug-resistant variants, or escape mutants, retain their virulence, and appear to play a major role in the virus' ability to eventually overwhelm the human immune system. A peculiarity of HIV is that it demonstrates an extremely high rate of both reproduction and mutation. As a direct consequence, drugs which demonstrate what would in any other context be regarded as high efficacy (99.9% reduction of viral load in plasma) have not been shown to be able to eliminate the virus from an individual's system. Further, an individual may have undetectable levels of virus as measured by viral load in plasma and biopsy of lymph nodes during treatment, and yet remain infected: once treatment is stopped, the viral rate of replication increases, and the viral load rebounds. In an attempt to obtain greater accuracy, the present inventors have used the most sensitive test methods available. Further, testing of lymph nodes is done by extracting an entire node as opposed to a biopsy sample.

Since escape mutants play such a significant role in the development of the disease, a major focus in current efforts to find a mode of treatment for AIDS is to develop strategies that feature multiple, highly effective, concurrent attacks on HIV in an effort to completely eradicate the virus from an individual's system. The only conclusive proof of effectiveness will be lack of rebound of the viral load in the individual's tissues over time.

At present, there is much interest in trying various combinations of two, three or even four drugs simultaneously. However, it has been admitted that the number of "promising" drugs is "almost astronomical". See Antiviral Therapy for Human Immunodeficiency Virus Infections, E. De Clercq, Clinical Microbiology Reviews, 8:2, Am. Soc. for Microbiology (April 1995).

A triple drug combination involving the use of AZT, 3TC and protease inhibitors has been suggested for the treatment of HIV-1 infection and eradication of the virus. The efficacy of this combination is thought to originate from the potency of the protease inhibitors and the mechanism of action of the AZT/3TC combination in inhibiting the rebound of resistant mutants. However, neither the protease inhibitors nor 3TC easily penetrate to certain organs such as lymph nodes and the brain, and the combination of protease inhibitor, AZT and 3TC apparently does not completely eradicate HIV-1 in macrophages or in quiescent cells, which are major reservoirs of HIV-1. Further, patients who have interrupted therapy using AZT, 3TC and protease inhibitors and then rebounded cannot be treated as effectively with the same combination because they develop resistant mutants.

Hydroxyurea has been widely used over the last three decades for the treatment of leukemia, sickle cell anemia, and has more recently been suggested for use in the treatment of HIV infections, see Hydroxyurea as an Inhibitor of Human Immunodeficiency Virus-Type 1 Replication, F. Lori, et al., Science 266:801–805 (1994); possibly in combination with a nucleoside analog such as AZT, ddI, or ddC, although it has been admitted that clinical trials using hydroxyurea alone or in combination with nucleoside analogs will be essential to assess the actual impact of use of hydroxyurea in HIV-1 impacted patients. Hydroxyurea and AIDS: An Old Drug Finds a New Application? F. Lori and R. Gallo, Aids Research and Human Retroviruses Vol. 11, No. 10 Mary Ann Liebert, Inc. (1995). EPO patent publication 94918016.0 filed May 17, 1994 and corresponding to U.S. Ser. No. 08.065,814, filed May 21, 1993, which is incorporated herein as if set forth in full, describes the administration of hydroxyurea in combination with ddI, and has reported a therapeutic effect in that CD4+T-cell populations stabilized or increased in human volunteers. This result does not necessarily demonstrate that any of the individuals were cleared of the virus, because when any patient has stopped any therapy to date, an immediate rebound of viral load has occurred.

Hydroxyurea and nucleoside analogs such as ddI have potent effects on resting cells and macrophages (ref. Lori, PNAS 93 and Science 94; Goa-Wy; Agbaria R., Driscoll, J. S.,; Missuya, H.; J. Biol-Chem. Apr 29, 1994; 269(17); 12633-8; AU: Gao-W. Y.; Shirasaka, T.; Johns, D. G.; Broder, S.; Mitsuya, H.; J.Clin. Invest. 1993 May: 91(5): 2326-33) which one can speculate represents the route of initial infection during sexual, parenteral and vertical transmission, (1. SO: Science, Aug. 27, 1993:261(5125) 1179–81; 2. SO: J. Clin. Invest. 1994 November: 94(5): 2060–7 4. SO: J. Clin. Microbiol. 1995 Feb; 33(2); 292–7, 5. S: AIDS. May; 9, 1995(5): 427–34; 6. SO: J. Exp. Med. Apr. 1, 1996; 183(4): 1851–6), and this could represent an advantage of the proposed combination.

Protease inhibitors have received much attention recently in the press as being useful in combination with other drugs such as nucleoside analogs, most especially the combination of AZT and 3TC, to inhibit HIV replication enough to yield improved quality of life for AIDS patients. It has been reported that the viral load in the plasma of such patients is greatly reduced, but not necessarily eliminated, and that whenever treatment has been stopped, the patients have experienced an increase in viral load (rebound) within a matter of 2–3 days.

The present invention is based on the discovery that a combination of hydroxyurea, a nucleoside analog, and a protease inhibitor can be used to inhibit HIV in human beings, with greatly improved results in that viral rebound may be delayed for at least three to eight weeks or more. These results indicate that the combination may be used for the treatment of HIV infection and eradication of the virus. Again, this combination takes advantage of the potency of the protease inhibitors, especially Indinavir. The HU/nucleoside analog combination has a different mechanism of action from that of the AZT/3TC combination. Further, it has been shown that the combination of HU and the nucleoside analog ddI is unable to prevent the onset of mutant viral strains conferring resistance to ddI, but the mutants are still sensitive to standard doses of ddI in the presence of HU. In addition, HU can easily penetrate to the organs such as lymph nodes and the brain, and can completely block the replication of HIV-1 in macrophages. Yet a further advantage is that viruses which are resistant to ddI and which have escaped can be inhibited by the addition of HU. Consequently, patients who have interrupted the treatment can be repeatedly treated effectively with the combination of HU, ddI and protease inhibitors.

DETAILED DESCRIPTION OF THE INVENTION

Figure 1:
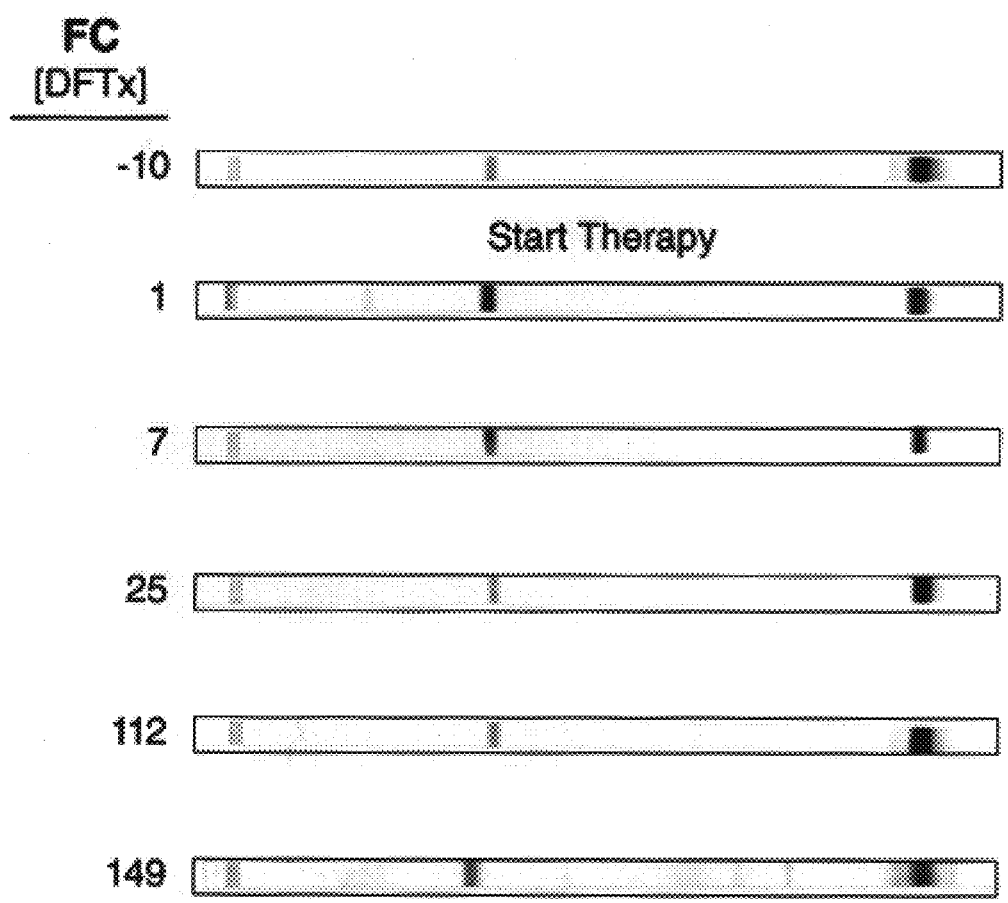
FIGS. 1–3 are the original Western Blot test results corresponding to the data in Tables 1–3, respectively.

Hydroxyurea is one of many inhibitors of ribonucleotide reductase, an enzyme known for catalyzing the reduction of ribonucleoside diphosphates to their deoxyribonucleoside counterparts for DNA synthesis. Other ribonucleotide reductase inhibitors include guanazole, 3,4-dihydroxybenzohydroxamic acid, N,3,4,5-tetrahydroxybenzimidamide HCl, 3,4-dihydroxybenzamidoxime HCl, 5-hydroxy-2-formylpyridine thiosemicarbazones, and n—(N)-heterocyclic carboxaldehyde thiosemicarbazones, 4-methyl-5-amino-1-formylisoquinoline thiosemicarbazone, N-hydroxy-N'-amino-guanidine (HAG) derivatives, 5-methyl-4-aminoisoquinoline thiosemicarbazone, diaziquone, doxorubicin, 2,3-dihydroxybenzoyl-dipeptides and 3,4-dihydroxybenzoyl-dipeptides, iron-complexed 2-acetylpyridine 5-[(2-chloroanilino)-thiocarbonyl]-thiocarbonohydrazone (348U87), iron-complexed 2-acetylpyridine-5-[(dimethylamino)thiocarbonyl]-thiocarbonohydrazone (A1110U),2'-deoxy-2'-methylenecytidine 5'-diphosphate (MdCDP) and 2'-deoxy-2', 2'-difluorocytidine 5'-diphospahte (dFdCDP), 2-chloro-9-(2-deoxy-2-fluoro-β-D-arabinofuranosyl)-adenosine (Cl-F-ara-A), diethyldithiocarbamate (DDC), 2,2'-bipyridyl-6-carbothioamide, phosphonylmethyl ethers of acyclic nucleoside analogs, [eg. diphosphates of N-(S)-(3-hydroxy-2-phosphonylmethoxypropyl and N-2-phosphonylmethoxyethyl) derivatives of purine and pyrimidine bases], nitrosourea compounds, acylclonucleoside hydroxamic acids (e.g., N-hydroxy-n -(2-hydroxyethoxy)-1 (2H)-pyrimidineacetamides 1-3, and 2-acetylpyridine 4-(2-morpholinoethyl)thio-semicarbazone (A723U)).

Hydroxyurea has been widely used in cancer therapy as a broad spectrum antineoplastic drug (R. C. Donehower, *Seminars in Oncology* 19:3 (Suppl. 9), 11 (1992)). Hydroxyurea is readily absorbed after oral ingestion, rapidly distributed in the body fluids, including the cerebrospinal fluid, and enters cells efficiently by passive diffusion (Id.). Its toxic effects are less profound and easier to control than other chemotherapeutic drugs (Id.).

In human chemotherapy, hydroxyurea is currently administered using two basic schedules: (a) a continuous daily oral dose of 20–40 mg per kg per day, or (b) an intermittent dose of 80 mg per kg per every third day. Either schedule could be used in the treatment of viral infections. Given the present invention, lower dosages of hydroxyurea may also be effective in treating HIV infections. Hydroxyurea is classified as a mildly toxic drug and does not cause immunodepression. Myelotoxicity is hydroxyurea's dose-limiting toxicity. However, such toxicity can be easily monitored and it is constantly and rapidly reversible after decreasing the dose or suspending the treatment (Donehower, R. C., *Semin. Oncol.* 19:11 (1992). By monitoring simple parameters such as peripheral cell counts, hydroxyurea can be administered for years,and sometimes for decades.

A second member of the combination of the present invention is a nucleoside analog, such as the 2',3'-dideoxyinosine (ddI) used in the Examples. Nucleoside analogs are a class of compounds known to inhibit HIV, and ddI is one of a handful of agents that have received formal approval in the United States for clinical use in the treatment of AIDS. See Clinical Microbiology Reviews, Supra, p. 200. Like zidovudine (3'-azido-2', 3'-dideoxythymidine or azidothymidine [AZT], zalcitabine (2',3' - dideoxycytidine [ddC], and stavudine (2',3' -didehydro-2',3'-dideoxythimidine [D4T], ddI belongs to the class of compounds known as 2',3' -dideoxynucleoside analogs, which, with some exceptions such as 2',3'-dideoxyuridine [DDU], are known to inhibit HIV replication, but have not been reported to clear any individual of the virus.

Currently, antiviral therapy requires doses of ddI at 500 mg per day for an adult human. Similar dosages may be used in the present invention. However, use of the combination drugs may increase the effectiveness of these nucleoside phosphate analogs so that they can be used at lower dosages or less frequently.

Of the potential protease inhibitors, compounds such as hydroxyethylamine derivatives, hydroxyethylene derivatives, (hydroxyethyl)urea derivatives, norstantine derivatives, symmetric dihydroxyethylene derivatives, and other dihydroxyethylene derivatives have been suggested, along with protease inhibitors containing the dihydroyeth-ylene transition state isostere and its derivatives having various novel and high-affinity ligands at the $P_2$ position, including 3-tetrahydrofuran and pyran urethanes, cyclic sulfolanes and tetrahydrofuranylglucines, as well as the $P_3$ position, including pyrazine amides. In addition, constrained "reduced amide"-type inhibitors have been constructed in which three amino acid residues of the polypeptide chain were locked into a γ-turn conformation and designated γ-turn mimetics. Other alternatives include penicillin-derived compounds, non-peptide cyclic ureas. At present, the inventors have no basis for distinguishing among the many potential protease inhibitors that may be used in combination with HU and a nucleoside analog. The protease inhibitor used in the Examples was Indinavir sulfate, available as Crixivan™ capsules from Merck & Co., Inc, West Point, Pa.

Suitable human dosages for these compounds can vary widely. However, such dosages can readily be determined by those of skill in the art. For example, dosages to adult humans of from about 0.1 mg to about 1 g or even 10 g are contemplated.

The combination of compounds of the present invention may be administered by any conventional route. Administration may be oral, intravenous, intraperitoneal, intramuscular, subcutaneous, transdermal, transmucosal (e.g., by inhalation or by means of a suppository), or by any other suitable route. Administration orally in a physiologically acceptable buffered solution is preferred. The buffered solution may be used for one or more members of the combination, while the other member or members may be administered in another form.

The particular dosage, toxicity, and mechanism for delivery of the individual of drugs of the present invention are either already known, or can be readily determined by conventional empirical techniques, as can dosages for the combination. The combination may result in the ability to use lower amounts of one or more of the constituents. This aspect of the invention may be particularly valuable with respect to the protease inhibitors, which generally are poorly soluble in water and have poor bioavailability. The present invention may address this problem in part by allowing lower dosages. The presently preferred dosage range for HU is 100–300 mg three times a day (TID), for ddI the preferred range is 100–300 mg twice a day (BID), and for Indinavir is 800 mg TID, assuming an adult weighing about 70 kg. One of ordinary skill in the art will recognize that different dosages and intervals may be appropriate. In the case of children, dosages wold tend to be lower due to their smaller mass. This combination would be expected to be particularly useful for children, as the HIV infection tends to result in more brain damage in children, and this combination has good effectiveness in crossing the blood-brain barrier.

The present invention may be used before and after acute infection, before seroconversion, and after seroconversion. In particular, the data presented herein demonstrates an early treatment of the infection that may result in a profound modification of the natural evolution of the HIV-1 infection. Further, the combination might be administered prophylactically to high-risk individuals.

In addition, the present combination allows for variation in the mode of treatment over time. The protease inhibitors are known known to be most useful in certain types of activated T-cells that are actively producing virus. They are less effective in quiescent cells. The triple combination could be used only in the initial phase of therapy until the viral load is undetectable in the plasma (less than 200 copies per milliliter) for longer than 2 months. At this point, the protease inhibitors have very likely accessed all the virus producing cells in the reservoirs they can access and have blocked active replication of the virus. Following this phase, the HU/nucleoside analog combination can be used for therapy until the virus is completely eliminated from the body. Depending on the status of the patient, the time of the treatment can be from several months to lifelong.

Another mode of treatment would be to deliberately activate certain types of quiescent cells during intensive triple combination therapy. Certain quiescent cells do not express HIV-1 proteins, and act as particularly stubborn reservoirs for the virus. In these cells, the HIV-1 DNA is integrated and both gene expression and virus production is only activated together with the activation of the cells. The cells may remain dormant for years before they spontaneously activate, and begin producing virus particles with the same ferocious reproductive rate and mutation rate as the original, acute infection. None of the presently known drugs can eliminate integrated viral DNA. This difficulty could be overcome if these cells were activated during effective combination therapy. The cells could be activated by vaccination against any of a number of diseases known to activate such cells, including, for example, HIV-1, Hepatitis B, Influenza, and Polio vaccination. HIV-1 genetic immunization is preferred, as disclosed in U.S. Ser. No. 60/604, 627, filed Feb. 21, 1996. Such activation should preferably take place after the elimination of active virus production (that is, after the patient's viral load is undetectable for at least 2 months). Repeated activation would be helpful to ensure that all quiescent cells harboring HIV-1 DNA had been activated.

SUMMARY OF THE INVENTION

It is an object of the present invention to provide a method of inhibiting the replication of retroviruses such as HIV-1, HIV-2, HTLV-1 and HTLV-2 in human cells. A further object of this invention is to provide a treatment for HIV infections that reduces the presence of the virus in both plasma and the lymphoid system, and which inhibits viral rebound after cessation of treatment. It is yet a further object of this invention to provide a method of treating HIV infection which is effective in the very early, as well as later, stages of infection. Yet another object of this invention is to provide a treatment for HIV which relatively less expensive and has relatively low toxicity, therefore increasing its suitability for widespread use in a large population. An even further object of this invention is to provide a method of activating quiescent cells harboring integrated viral DNA under controlled conditions for the purpose of eliminating the integrated viral DNA.

The present inventors have found that the combination of hydroxyurea (HU), 2',3'-dideoxyinosine (ddI) and a protease inhibitor is capable of reducing the presence of the virus in both plasma and lymph nodes, as well as seminal fluids, the typical mode of transmission of the disease. An advantage of the present invention is that it can be used very early after infection to prevent seroconversion of a person infected with HIV, as well as after seroconversion. A further advantage is that the combination has relatively low toxicity, and may be suitable as a long-term treatment for chronic infection for a wide range of individuals. Yet another advantage is that, in addition to reducing the viral load in plasma and in the lymph nodes to undetectable levels, the present invention has been shown to inhibit viral rebound after treatment is stopped.

These and other objects and advantages of the present invention will become apparent through the text and examples herein.

The following Examples are presented for the purpose of illustrating the practice of the present invention. They do not limit the invention, or the claims which follow.

EXAMPLES

A key step of HIV-1 infection of lymphocytes is the conversion of the viral RNA genome into double-stranded DNA by the action of HIV-1 RT. Viral DNA synthesis differs in different states of infected lymphocytes. In quiescent cells, viral DNA synthesis can be initiated as efficiently as in activated cells. However, in contrast to the activated cells, DNA synthesis in quiescent lymphocytes may terminate prematurely (J. A. Zack, et al., *Cell* 61:213 (1990); J. A. Zack, et al., *Virology* 66:1717 (1992)) producing no HIV-1 progeny (Zack, et al, supra; M. Stevenson, et al., *EMBO J.* 9:1551 (1990); M. I. Bukrinsky, et al., *Science* 254:423 (1991)). This process results in a pool of unintegrated viral DNA (Stevenson, et al., supra; Bukrinsky, et al., supra), which can remain latent in both in vitro infected quiescent peripheral blood lymphocytes and in vivo infected resting peripheral blood lymphocytes (Zack, et al., supra, 1990 & 1991; Stevenson, et al., supra; Bukrinsky, et al., supra). Activation of these cells can rescue HIV-1 DNA, leading to integration and production of viral progeny (Id.). Incomplete viral DNA has also been found associated with HIV-1 mature infectious particles, but the biological role of this DNA is unclear (F. Lori, et al., *J. Virol.* 66:5067 (1992); D. Trono ibid. 66:4893 (1992)).

Example 1 illustrates the various methods that can be used to quantitate the replication of the HIV-1. A variety of different tests with different sensitivities are currently in use, particularly since researchers have found that older screening methods with a sensitivity of <400 copies per milliliter plasma are simply not sensitive enough to tell whether a dangerous infection continues to exist in the individual. It has also been demonstrated that lymphoid tissues are the major reservoirs of HIV-1,(See Pantaleo G., Graziosi C., Demarest, J. F., Butini. L., Montroni, M., Fox, C. H., Orenstein, J. M., Kotler D. P., Fauci, A. S. HIV infection is active and progressive in lymphoid tissue during the clinically latent stage of disease. Nature 362(6418): 355–358 (1993) therefore, new detection methods for HIV-1 RNA and DNA have been developed and applied to the lymph tissues. Of the newer methods, the most sensitive used herein is the nested PCR assay detecting HIV-1 DNA (sensitivity: one copy of virus per sample) applied to one half of a lymph node. Another new method is the in situ hybridization detection of HIV-1 RNA, (See Fox C. H., Cottler-Fox, M. In situ hybridization for the detection of HIV RNA in cells and tissues. Current Protocols in Immunology (Coligan, J., Kruisbeek, A., Margulies, D., Shevack E., Strober, W. eds), Wiley, N.Y., 1993; and Fox C. H., Cottler-Fox, M. In situ hybridization in HIV research. Microscopy Research and Technique 25:78–84, 1993.) can be applied to the other half of the lymph node. A more typical sample size as reported in the current literature would be obtained via biopsy of the lymph node rather than its complete surgical removal.

Example 1

HIV Replication

Inguinal lymph nodes were surgically removed and cut in half along a longitudinal axis. One part was fixed in formalin for in situ hybridization and the other part was frozen in liquid nitrogen. The frozen tissue was homogenized and its DNA was extracted. HIV-1 DNA was amplified by a highly sensitive polymerase chain reaction (PCR assay), described in detail in Methods in Molecular Biology, Vol. 15: PCR Protocols.

PCR SK primers SK38 and SK39 are available from Perkin-Elmer, Norwalk, CT. The PCR-reaction mixture contained the following: 500 ng of genomic DNA, 0.2 mM of each primer, 100 µM of each nucleoside triphosphate, 1.5 mM $MgCl_2$, 20 mM Tris-HCl (pH 8.4), 50 mM KCl and 1 units of Taq DNA polymerase (Boheringher Manheim Corporation, Indianapolis, Ind.) in a final volume of 100 µl. The cycle conditions were 95° C. for 3 minutes, 50 times (94° C. for 1.30 min, 56° C. for 1.00 min and 72° C. for 1.00 min) and 72° C. for 10 minutes.

The following PCR RT primers were designed and used by the inventors: sense-primer RT-F1 (5-GGACCTACACCTGTCAACAT-3, nucleotides 127 to 146 of HXB2 pol gene Sequence 1) and antisense-primer RT-R8 (5-CATTTATCAGGATGGAGTTCATA-3, nucleotides 886 to 908 of HXB2 pol gene Sequence 2).

The PCR-reaction mixture contained the following: 500 ng of genomic DNA, 0.2 µM of each primer, 100 µM of each nucleoside triphosphate, 2 mM $MgCl_2$, 20 mM Tris-HCl (pH 8.4), 50 mM KCl and 1 units of Taq DNA polymerase (Boheringher Manheim Corporation, Indianapolis, Ind.) in a final volume of 100 µl.

The cycle conditions were 95° C. for 3 minutes, 50 times (94° C. for 1.30 min, 56° C. for 1.30 min and 72° C. for 1.30 min) and 72° C. for 10 minutes.

Hybridization primers:
RT-F7 gene Sequence 3 GGATGGAAAGGATCACCAGC
RT-R6 gene Sequence 4 TACTAGGTATGGTAAATGCAGT
NESTED-PCR (THIS CAN INCREASE THE SENSITIVITY FURTHER)
sense-primer RT-F5 (5-CAGGAATGGATGGCCCAAAAGT-3, nucleotides 233 to 254 of HXB2 pol gene Sequence 5)
antisense-primer RT-R12 (5-TTCATAACCCATCCAAAG-3, nucleotides 874 to 891 of HXB2 pol gene Sequence 6).

PCR conditions were 1 µl from the first PCR reaction, 0.4 µM of each primer, 200 µM of each nucleoside triphosphate, 1.5 mM $MgCl_2$, 10 mM Tris-HCl, 50 mM KCl, and 1 unit of Taq DNA polymerase (Boheringher), in a final volume of 50 µl.

The cycle conditions were 95° C. for 3 minutes, 45 times (94° C. for 30 sec., 55° C. for 30 sec. and 72° C. for 30 sec.), and 72° C. for 10 minutes.

The DNA from PCR reaction was separated on an agarose gel and visualized by Ethidium Bromide staining. Polaroid pictures were taken. To increase the sensitivity at least 100 fold, the DNA was blotted to nitrocellulose paper and hybridized with a fluorecents labeled oligonucleotide according to the manufacturer protocol (ECL 3-oligolabelling and detection systems. Amersham Life Science, Little Chalfont, England).

Primer F1 was previously described by Xiping W, Ghosh S, Taylor M, Johnson V, Emini E, Deutusch P, Lifson J, Bonhoeffer S, Nowak M, Hahn B, Saag M, Shaw G. Viral dynamics in human immunodeficiency virus type 1 infection. Nature 1995;373:117–122; Primer F5 was described by Saag, M. S., Emini, E. A., Laskin, O. L., Douglas, J., Lapidus, W. I., Schleif, W. A., Whitley, R. J., Hildebrand, C., Byrnes, V. W., Kappes, J. C., Anderson, K., Massari, F., Shaw, G., and the L-697 working group. A short-term clinical evaluation of L-697,661, a non-nucleoside inhibitor of HIV-1 reverse transcriptase. L-697,661 Working Group. N. Engl. J. Med. 1993;329:1065–72.

Genomic DNA extraction from lymph nodes. Extraction of DNA from whole tissue was done by using a DNA extraction kit available from Stratagene, La Jolla, Calif., according to the manufacturer's instructions. The only modification was that the frozen lymph nodes were first ground to a powder in a porcelain mortar under liquid nitrogen, and then the powder was transferred into a Wheaton Potter-Elvehjem tissue grinder and homogenized in a lysis buffer. Incubation with protonase was done at 37° C. overnight.

Viral load quantitation by NASBA™ in semen. Quantitation of HIV-1 RNA in semen was performed by using a NASBA™ HIV-1 RNA QT kit available from Organon Teknika, Netherlands, according the the manufacturer's protocol. Briefly, 200 µl of semen were mixed with 1.8 ml of lysis buffer and frozen until use. Nucleic acids were extracted using a guanidine thiocyanate-silica based method (Boom, R., Sol, C. J. A., Salimans, M. M. M., Jansen, C. L., Wertheim-van Dillen, P. M. E., van der Noordaa, J. (1990) A rapid and simple method for purification of nucleic acids. J. Clin. Microbiol. 28:495–503 and van Gemen, B., Kievets, T., Schukkink, R., van Strijp, D., Malek, L. T., Sooknanan, R., Huisman, H. G., Lens, P. (1993) Quantitation of HIV-1 RNA in plasma using NASBA™ during HIV-1 primary infection. J. Virol. Meth. 43: 177–188.) Amplification of the target HIV-1 RNA by NASBA™ was performed with primers specific for the gag region of the HIV-1 genome (Kievits, T., van Gemen, B., van Strijp, D., Schukkink, R., Dircks, M., Adriaanse, H., Malek, L., Sooknanan, R., Lens, P (1990) NASBA™ isothermal enzymatic in vitro nucleic acid amplification optimized for the diagnosis of HIV-1 infection. J. Virol. Meth. 35: 273–286, and van Gemen, B., van Beuningen, R., Nabbe, A., van Strijp, D., Jurriaans, S., Lens, P., Kievits, T. (1994) A one-tube quantitative HIV-1 RNA NASBA nucleic acid amplification assay using electrochemiluminescent (ECL) labeled probes. J. Virol. Meth. 49: 157–168.

Example 2

Figure 2:
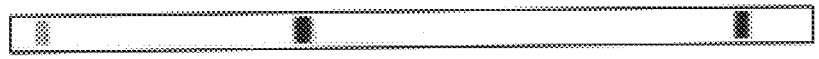
Figure 2:
Figure 2:
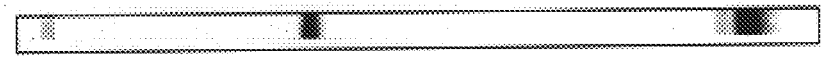
Figure 2:
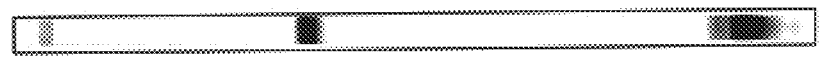
Figure 2:
Figure 2:
Figure 2:
Figure 2:
Figure 3:
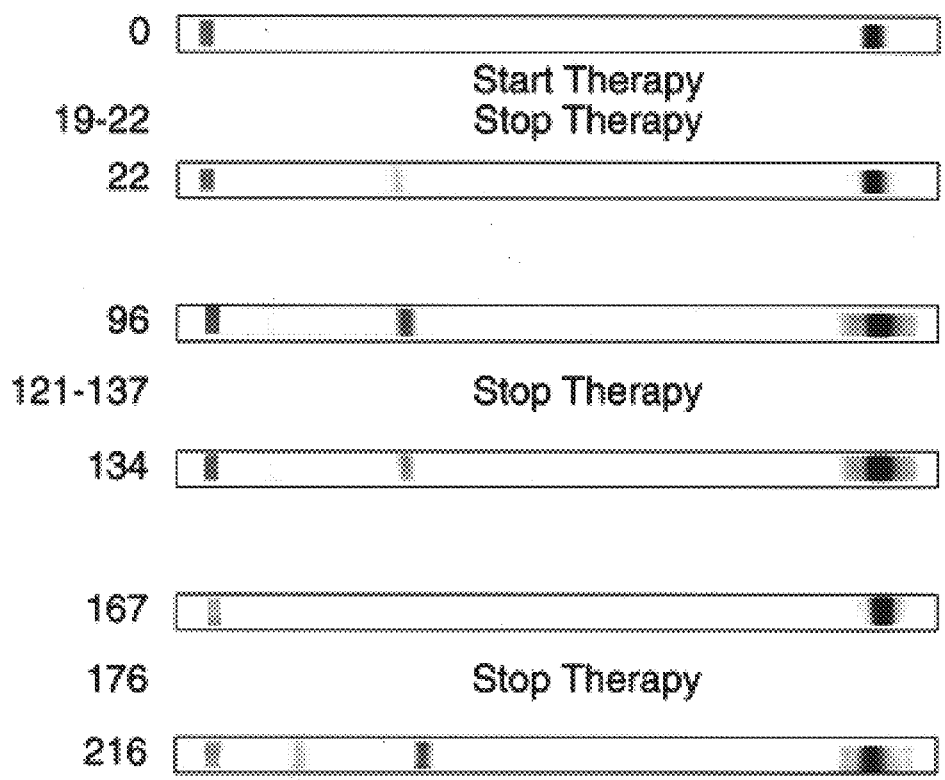
Figure 3:
Figure 3:
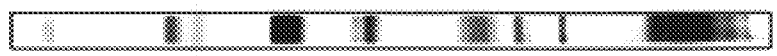

Six individuals were treated with the combination of hydroxyurea, a nucleoside analog, and a protease inhibitor. The general course of treatment was HU, 60 mg/kg TID; ddl, 200 mg BID, Indinavir 800mg/TID. Three of them were treated within 4–7 weeks following primary infection and before seroconversion, that is, when the Western Blot was not completely positive. Three patients were treated from <1 year to >5 years after seroconversion. In all the individuals the levels of plasma viremia became undetectable within 3–25 weeks after treatment. All the data is shown below in Tables 1–6, each of which is further identified by a two-letter code. FIGS. 1–3 contain the corresponding Western Blot information for three of the patients.

Three individuals began treatment within 14 to 31 days following the onset of symptoms (DFOS) of a primary HIV-1 infection and before seroconversion. In all of these individuals, the levels of plasma viremia became undetectable within 73 to 136 DFOS (with a drop of viremia between 2.7 to 3.4 logs) and remained undetectable during the course of treatment. None of these patients fully seroconverted, despite a documented exposure to HIV-1 ranging between 163 and 236 days. Their Western Blot patterns remained almost unaltered during the course of the observation. See Tables 1–3, for results of BM, FC, and SH, and FIGS. 1–3 for the original and subsequent Western Blot results. Moreover, a significant, sharp increase of the CD4/CD8 ratio and CD4 count was observed in all three patients. Lymph nodes were collected from these patients at different time points. Significant HIV-1 RNA was detected by in situ hybridization, by screening over 40 million cells, in only one patient (FC).

The first node of FC was analyzed 8 weeks after beginning treatment, while the virus was still detectable in the plasma, and HIV-1 RNA was mainly associated to the follicular dendritic cells. At this time, the CD4 count and CD4/CD8 ratio was normal. Later, when HIV-1 was no longer detectable in the plasma, another inguinal lymph node was obtained and analyzed as before. No HIV-1 RNA was detected at that time. Again, DNA was extracted from the half of the lymph node which was frozen and tested by PCR analysis using 2 different primers and also a nested primer (sensitivity of this test is to one copy of viral DNA per sample). The PCR was positive, indicating that FC had at least one copy of HIV-1 DNA in the lymph node. See Table 1.

In patient SH, HIV-1 became undetectable in the plasma at 105 days after treatment had begun, with a decrease in viremia of 3.2 log from the baseline. The CD4 counts and CD4/CD8 ratios increased promptly after treatment began (from 0.33 to 0.95 in 33 days). In two consecutive analyses, no RNA was detected in the lymph nodes, but at least 1 copy of viral DNA was detected at 176 days from the onset of symptoms and 145 days from the start of treatment. No significant changes were observed in the Western blot profile of SH during the course of the follow-up. See Table 2.

The third patient (BM, see Table 3) was treated starting 7 weeks after the probable date of infection. Between 19 and 22 days after starting the therapy, he interrupted the treatment for three days, concomitantly with an episode of orchitis. A rebound of plasma viremia was monitored immediately after the three day suspension. Therapy was started again, and at about week 5 after initiating treatment, HIV-1 was undetectable in the plasma. At week 16, an inguinal lymph node was analyzed and 2 RNA producing cells were found out of 44 million cells screened. At week 17, treatment was again interrupted, this time due to an episode of acute hepatitis A. Despite the massive immune stimulation due to this concomitant viral infection, this individual did not show any sign of viral rebound during the following two weeks, although a positive value was found but could not be confirmed. The same week, BM again started taking the therapy. After an additional 4–5 weeks of therapy taken at irregular intervals, the patient discontinued treatment altogether. Another lymph node was obtained 18 days following final suspension of therapy, and 2 RNA producing cells were found out of a total of 44 million cells screened. No DNA could be detected in this lymph node, even after repeated nested PCR analysis. The plasma tested positive for RNA 40 days after treatment suspension at very low levels, but this positivity could not be confirmed. During all the course of the follow-up, cell counts did not significantly change, and the Western blot profile remained practically unchanged.

Semen of patients FC, SH and BM was tested at 141, 176, and 214 days from onset of symptoms, respectively, and HIV-1 RNA was undetectable by NASBA (sensitivity <400 copies/ml). Similarly, the semen of the other patients, when tested, showed negative results.

The viral load variations in the plasma and the changes in the CD4 and CD8 absolute/relative counts of the three patients who were treated after seroconversion did not differ significantly from those who were treated before seroconversion. Patients TD and LF showed sharp increases in CD4 counts back to normal levels and their CD4/CD8 ratios now range between 1.1 and 1.4. See Tables 4 and 5. The one patient who had the longest (>5 years) infection before therapy and started with the lowest CD4 count (330), LJ, showed marked improvement also, but progress was slower. This patient became virus negative in the plasma only after 25 weeks of treatment, and the increase of the CD4/CD8 ratio was slower and less significant than in the other individuals. The CD4/CD8 ratio remains at about 0.4 at this time. See Table 6.

The patient who had been seropositive for the longest period of time, LJ, (See Table 7) had low but detectable levels of HIV-1 RNA and proteins in the lymph node after 27 weeks of treatment.

Patient TD had been seroconverted for approximately 6 months before treatment had begun. Patient TD currently shows no traces of viral DNA or RNA in the sperm, serum, or lymph nodes. This patient has had a history of hepatitis infection in March, 1996.

These data indicate that the combination of hydroxyurea, ddI and a protease inhibitor present a potent new combination that can rapidly clear the virus from plasma and lymph nodes, and inhibit viral rebound after cessation of treatment. Further, this combination blocks HIV-1 replication in the lymphoid system and, at least in one case, shows hope for HIV-1 eradication.

In addition, these data indicate that HIV-1 infection is treatable as an emergency disease. Patients should be tested not for seroconversion, but for free virus particles in the blood if there are any symptoms or suspicion of infection, and treated immediately with the combination therapy before seroconversion takes place. The present invention will eliminate the free virus, block new infections, restore the immune system, and may have eliminated virus integration in millions of cells. This method would also be economical, as treatment would be begun earlier and be of shorter duration than treatment for people with chronic infections. The present results show that the patients treated early restored the normal lymphocyte status in short periods of time (see CD4+cells and CD4/CD8 ratio). However, the patient that had been infected for 5–9 years (LJ, see Table 6) could not as rapidly restore the lymphocyte status even after 9 months of therapy, even though virus production was completely blocked. This demonstrates that the in vivo clearance rate cannot be generalized for all treatments that apparently reduce the presence of virus in plasma. Further, the same patient, unlike the patients with fresh infections, did not demonstrate restoration of the T-cell repertoire (CD4 counts and CD4/CD8 ratios) to the normal levels. This result indicates that late in the infections, T-cells do not turn over at the same rate as they did earlier, and regeneration of T-cells may be impaired. It further suggests early treatment.

The present results also indicate that a method of eliminating quiescent cells, that is, cells which have integrated viral DNA, but do not currently express the genes or produce virus. HIV-1 DNA was measured in the lymphocytes of the patients with a highly sensitive nested PCR able to detect as little as 1 copy of viral DNA. Two patients in this group had no detectable HIV-1 DNA in the lymphoid organ and 3 had detectable DNA. Other investigators have also reported (in all cases) detectable DNA in the lymphoid organs even in the absence of virus producing cells (Markovitz, Retrovirus Conference, 1997) The present inventors are not aware of any other patients other than the two in the present study (TD, BM) who have undetectable viral DNA in the lymphoid organs. The only common feature of these patients is that both experienced hepatitis infection. BM had Hepatitis A and TD had hepatitis B. Both infections are characterized by activation of cells which can harbor HIV-1 DNA. After activation, these cells can produce viral particles which will be mainly defective in the presence of protease inhibitors. HU and ddl will work at the early phase, inhibiting reverse transcription with two different mechanisms, consequently blocking both new infection and new DNA integration.

The present results also show that early treatment of individuals (BM, SH, FC and TD, LF) infected by HIV-1 led to a profound modification of the natural evolution of HIV-1 infection.

First, HIV-1 became and remained undetectable in the plasma. The implication of this result is highly relevant. In fact, only 8% of individuals with less than 4,350 copies of RNA per milliliter of blood plasma soon after infection developed AIDS 5 years after infection, whereas 62% of those with values greater than 36,270 progressed to AIDS (Mellors, J. W. et al., Science 272(5265) 1167–1170, 1996). In the ACTG 175 study, a decrease of 1.0 log in the concentration of HIV-1 RNA from the baseline after therapy with nucleoside analogs in patients with CD4 counts between 200 and 500 per cubic millimeter was associated significantly with a 65% reduction in the risk of AIDS or death (N.Engl. J. Med. Oct. 10, 1996:335(15):1091–8). All the patients analyzed here had high levels of viral replication (between 89,390 and 487,955 copies/mL) before the treatment and this load was decreased between 2.7 and 3.4 logs, that is, below 200 copies/mL.

Second, also in the lymph node compartment, which has been described as the major reservoir of the virus, only traces of HIV-1 RNA and/or DNA could be inconstantly detected. In particular, follicular dendritic cell-associated HIV-1 found in patient FC 57 days following treatment rapidly disappeared 70 days later, indicating the rapid clearance of follicular dendritic cell-associated HIV-1 following this therapy.

Third, CD4 counts increased promptly to normal levels and CD4/CD8 ratios were normalized in patients LF, TD, FC, SH, BM, whereas these values typically fail to increase to normal.

Fourth, lack of a full seroconversion in 3 of these patients treated prior to seroconversion suggests that the replication of the virus has at least been reduced to a minimum. Of particular interest is the observation that all of the above considerations hold true even after the treatment has been suspended in one of the patients. Despite a possible smoldering expression of viral RNA, DNA was repeatedly undetectable in the lymph nodes, even with a methodology able to detect a single copy of viral DNA.

Fifth, we have recently shown on an animal model (unpublished) that an early treatment with ddl and ddl with hydroxy urea, although unable to prevent the infection of pigtail macaques by a lethal dose of SIV, reduced the viral load and rescued the animals from death. This also demonstrates that early, effective treatment can completely change the course of lentivirus infection.

The combination of hydroxyurea, 2',3'-dideoxyinosine (ddl) and Indinavir during the acute primary phase of infection resulted in a very potent, long lasting block of HIV-1 replication in the blood, lymph nodes and semen and in the restoration of the immune system. In one patient, the treatment was suspended without substantial viral rebound or seroconversion.

While particular embodiments of the invention have been described in detail, it will be apparent to those skilled in the art that these embodiments are exemplary rather than limiting, and the true scope of the invention is that defined by the claims that follow.

TABLE 1

VIRAL LOAD, LYMPHOCYTE AND SEROCONVERSION ANALYSES FOR PATIENT FC

Infected: End July beginning of August according to Heiko 3 day break in therapy: Sept 15–18, 1996

Therapy begun 2 Sept. 96

HU 400 mg TID
ddl 200 mg BID
INDINAVIR 800 mg TID

| VIRAL LOAD IN THE BLOOD | | | | | VIRAL LOAD IN THE LYMPH NODE | | | | | |
|---|---|---|---|---|---|---|---|---|---|---|
| D/M/Y | bDNA/PCR | PCR/RIGHT | | | D/M/Y p24 antigen expression | HIV-RNA in situ | | HIV DNA PCR | SEMEN | VIRAL LOAD |
| 23.8.96 | 800,000 | | | | | | | | | 07.01.97 |
| 26.8.96 | 1,280,000 | | | | 29.10.96 | | | | | <400 copies/ml |
| 2.9.96 | 785,000 | 487955 | start | 2–9 | FDC | Cells | FDC | Cells | | |
| 9.9.96 | 37,000 | 22497 | stop | 15–18 | – | – | + | (few) + | Not detected | |
| 20.9.96 | 21,000 | 13929 | | | 07.01.97 | | | | | |
| 27.9.96 | 500 | 5919 | | | – | – | – | – | positive | |
| 29.10.96 | 500 | 673 | | | | | | | | |
| 18.11.96 | 400 | <200 | | | | | | | | |
| 23.12.96 | 400 | <200 | | | | | | | | |
| 6.1.97 | | <200 | | | | | | | | |
| 14.01.97 | 500 | | | | | | | | | |
| 29.1.97 | | <200 | | | | | | | | |

LYMPHOCYTE POPULATION ANALYSIS

| D/M/Y | Lymph. | B.Ly | T-Ly | CD4 | CD4 % | CD8 | CD8 % | Ratio |
|---|---|---|---|---|---|---|---|---|
| 26.10.96 | 2,543 | 200 | 2,010 | 1,220 | 48 | 970 | 38 | 1.26 |
| 18.8.96 | 1,336 | 110 | 900 | 380 | 28 | 680 | 5 1 | 0.56 |
| 23.8.96 | 1,548 | 80 | 1,020 | 330 | 21 | 850 | 55 | 0.39 |
| 27.8.96 | 1,974 | 99 | 1,210 | 474 | 24 | 1,046 | 53 | 0.45 |
| 2.9.96 | 3,256 | 130 | 2,583 | 684 | 21 | 2,084 | 64 | 0.33 |
| 9.9.96 | 2,415 | 242 | 1,771 | 652 | 27 | 1,232 | 51 | 0.53 |

TABLE 1-continued

VIRAL LOAD, LYMPHOCYTE AND SEROCONVERSION ANALYSES FOR PATIENT FC

| | | | | | | | | | |
|---|---|---|---|---|---|---|---|---|---|
| 20.9.96 | 1,546 | 216 | 1,199 | 680 | 44 | 526 | 34 | 1.29 |
| 18.11.96 | 2,149 | 279 | 1,624 | 946 | 44 | 688 | 32 | 1.38 |
| 06.01.97 | 1,480 | 252 | 1,139 | 696 | 47 | 459 | 31 | 1.52 |
| 29.01.98 | 2,416 | 314 | 1,705 | 821 | 34 | 870 | 36 | 0.94 |

SEROCONVERSION BY WESTERN BLOT TEST

| Date | HIV 1 + 2 | gp160 | gp120 | p65 | p55 | gp41/43 | p32 | p24 | p18 |
|---|---|---|---|---|---|---|---|---|---|
| 19.08.96 | ± | ± | – | – | – | – | – | ± | – |
| 23.08.96 | ± | ± | ± | – | – | – | – | ± | ± |
| 02.09.96 | ± | ± | ± | – | – | – | – | ± | ± |
| 09.09.96 | ± | ± | ± | – | – | – | – | ± | ± |
| 27.09.96 | ± | ± | ± | ± | – | – | – | ± | ± |
| 23.12.96 | ± | ± | ± | ± | ± | ± | ± | ± | ± |

Table Legend:
1. Each table summarizes viral load, lymphocyte and, where applicable, seroconversion analyses for a single patient over time.
2. Dates are listed as day/month/year "D/M/Y".
3. Viral load was measured on the dates indicated by a contract laboratory ("bDNA/PCR") or by the inventor's laboratory ("PCR/RIGHT").
4. Results for tests for viral load in the lymph nodes were recorded as follows:
"p24 antigen expression": measured by antibodies against HIV protein p24 applied to a thin layer of lymnph node tissue.
"HIV-RNA in situ": measured by nucleotide binding to lymph node tissue.
"HIV DNA PCR": standard test for viral load. "Not detected" means not tested on that date.
"FDC": Follicular Dendritic Cells
"Cells": Lymph node cells generally.
5. Lymphocyte population analysis shows the complement of the patient's lymphocytes at the given dates.
"Lymph.": Total number of lymphocytes.
"B.Ly": Total number of B-lymphocytes.
"T-Ly": Total number of T-Lymphocytes.
"CD4" Total number of CD4+ lymphocytes.
"CD4 %": The percentage of total lymphocytes that are CD4+ lymphocytes.
"CD8": Total number of CD8+ lymphocytes.
"CD8 %": The percentage of total lymphocytes that are CD8+ lymphocytes.
"Ratio": The CD4+/CD8+ ratio.
6. Seroconversion was shown by Western Blot analysis. The patient's blood was screened for antibodies to the listed HIV proteins at the given dates.

TABLE 2

VIRAL LOAD, LYMPHOCYTE AND SEROCONVERSION ANALYSIS OF PATIENT SH

| Infection: The patient says he was | Therapy begun 27 July, 96 | | |
|---|---|---|---|
| infected June 96 | HU | 400 mg TID | |
| He went to hospital 15 July 96 with | ddI | 200 mg BID | |
| high fever | INDINAVIR | 800 mg TID | |

| VIRAL LOAD IN THE BLOOD | | | D/M/Y | VIRAL LOAD IN THE LYMPH NODE | | | | VIRAL LOAD SEMEN |
|---|---|---|---|---|---|---|---|---|
| D/M/Y | bDNA/PCR | PCR/RIGHT | | p24 antigen expression | HIV-RNA in situ | HIV DNA PCR | | |
| 19.7.96 | 199000 | | | | | | | 07.01.97 |
| 22.7.96 | 192000 | 319146 | 16.10.96 | | | | | <400 copies/ml |
| 26.7.96 | 3260000? | 871602 | | FDC | Cells | FDC | Cells | |
| 31.7.96 | 82310 | 143435 | | – | – | – | – | Not detected |
| 20.8.96 | | 3100 | 07.01.97 | | | | | |
| 23.9.96 | 500 | 918 | | – | – | – | – | positive |
| 25.10.96 | 500 | 266 | | | | | | |
| 28.11.96 | 500 | <200 | | | | | | |
| 12.12.96 | | <200 | | | | | | |
| 08.01.97 | 500 | | | | | | | |
| 29.1.97 | | <200 | | | | | | |

LYMPHOCYTE POPULATION ANALYSIS

| D/M/Y | Lymph. | B.Ly | T-Ly | CD4 | CD4 % | CD8 | CD8 % | Ratio |
|---|---|---|---|---|---|---|---|---|
| 19.7.96 | 1,578 | 170 | 1,250 | 520 | 33 | 870 | 55 | 0.60 |
| 26.7.96 | 1,778 | 120 | 1,400 | 410 | 23 | 1,190 | 67 | 0.34 |
| 2.8.96 | 2,040 | 220 | 1,570 | 590 | 29 | 1,140 | 56 | 0.52 |
| 20.8.96 | 1,911 | 230 | 1,450 | 590 | 31 | 1,010 | 53 | 0.58 |
| 17.9.96 | 2,012 | 302 | 1,549 | 804 | 40 | 845 | 42 | 0.95 |
| 25.10.96 | 1,816 | 182 | 1,412 | 672 | 37 | 708 | 39 | 0.95 |

TABLE 2-continued

VIRAL LOAD, LYMPHOCYTE AND SEROCONVERSION ANALYSIS OF PATIENT SH

| 12.12.96 | 1,742 | 244 | 1,352 | 645 | 37 | 627 | 36 | 1.03 |
| 14.01.97 | 2,424 | 267 | 1,798 | 776 | 32 | 970 | 40 | 0.80 |
| 29.01.97 | 2,133 | 299 | 1,527 | 661 | 31 | 832 | 39 | 0.79 |

SEROCONVERSION BY WESTERN BLOT TEST

| D/M/Y | HIV 1 + 2 | gp160 | gp120 | p65 | p55 | gp41/43 | p32 | p24 | p18 |
|---|---|---|---|---|---|---|---|---|---|
| 19.07.96 | ± | ± | − | − | − | − | − | − | − |
| 02.08.96 | ± | ± | − | − | − | − | − | ± | − |
| 20.09.96 | ± | ± | − | − | − | − | − | ± | − |
| 17.09.96 | ± | ± | ± | − | − | − | − | ± | − |
| 04.10.96 | ± | ± | ± | − | − | − | − | ± | − |
| 12.12.96 | ± | ± | ± | − | − | − | − | ± | ± |

TABLE 3

VIRAL LOAD, LYMPHOCYTE AND SEROCONVERSION ANALYSES FOR PATIENT BM

Infection 10 May 96  
Testis infection 10 July 96; stop therapy:  
12–19 July 1996  
Acute hepatitis A infection: stop therapy Therapy begun 27 June 96

26 Oct. 96  
Takes pills very irregularly  
Stops voluntarily treatment on December 20

HU 300 mg TID  
ddI 200 mg BID  
INDINAVIR 800 mg TID

VIRAL LOAD IN THE LYMPH NODE

| VIRAL LOAD IN THE BLOOD | | | | D/M/Y | | | | | VIRAL LOAD |
|---|---|---|---|---|---|---|---|---|---|
| D/M/Y | bDNA/PCR | PCR/RIGHT | | p24 antigen expression | | HIV-RNA in situ | | HIV DNA PCR SEMEN | |
| 21.06.96 | 12620 | 80041 | | | | | | | 07.01.97 |
| 9.7.96 | <500 | 1099 | stop (12–19) | FDC | Cells | FDC | Cells | | <400 copies/ml |
| 19.7.96 | 1134 | 5356 | rebound | 16.10.96 | | | | | |
| 19.6.96 | <500 | <200 | neg | − | − | − | 2 pos. in 44 million | Not detected | |
| 5.9.96 | <500 | <200 | | 01.7.97 | | | | | |
| 1.10.96 | <500 | <200 | stop 26 Oct | − | − | − | 3 pos. in 44 million | negative | |
| 29.10.96 | <500 | <200 | | | | | | | |
| 1.11.96 | | <200 | | | | | | | |
| 8.11.96 | <400 | 324; <200 | starts 11 Nov | | | | | | |
| 11.12.96 | <500 | <200; <200 | stop 20 Dec | | | | | | |
| 07.01.97 | <400 | <200; <200 | 2,5 wks a. stop | | | | | | |
| 16.01.97 | | 279; <200 | | | | | | | |
| 27.01.97 | <500 | 221; <200 | 5 wks a. stop | | | | | | |
| 7.2.97 | <500 | nd | | | | | | | |
| 14.2.97 | 700? | nd | | | | | | | |

LYMPHOCYTE POPULATION ANALYSIS

| D/M/Y | Lymph. | B.Ly | T-Ly | CD4 | CD4 % | CD8 | CD8 % | Ratio |
|---|---|---|---|---|---|---|---|---|
| 21.6.96 | 1,408 | 210 | 1,020 | 370 | 26 | 710 | 50 | 0.52 |
| 24.6.96 | 1,411 | 230 | 1,020 | 410 | 29 | 690 | 49 | 0.59 |
| 26.6.96 | 1,965 | 270 | 1,430 | 570 | 29 | 940 | 48 | 0.61 |
| 19.7.96 | 1,643 | 310 | 1,130 | 490 | 30 | 620 | 38 | 0.79 |
| 19.8.96 | 1,880 | 280 | 1,330 | 660 | 35 | 730 | 39 | 0.90 |
| 1.10.96 | 1,587 | 238 | 1,152 | 571 | 36 | 540 | 34 | 1.06 |
| 1.11.96 | 1,907 | 305 | 1,426 | 572 | 30 | 801 | 42 | 0.71 |
| 11.12.96 | 2,304 | 392 | 1,553 | 991 | 43 | 968 | 42 | 1.02 |
| 7.1.97 | 2,145 | 429 | 1,471 | 751 | 35 | 686 | 32 | 1.09 |
| 29.1.97 | 1,961 | 412 | 1,302 | 628 | 32 | 588 | 30 | 1.07 |
| 7.2.97 | 2,306 | 369 | 1,591 | 738 | 32 | 853 | 37 | 0.87 |
| 14.02.97 | 2,232 | 379 | 1,482 | 670 | 30 | 761 | 35 | 0.86 |

SEROCONVERSION BY WESTERN BLOT TEST

| Date | HIV 1 + 2 | gp160 | gp120 | p65 | p55 | gp41/43 | p32 | p24 | p18 |
|---|---|---|---|---|---|---|---|---|---|
| 11.6.96 | ± | − | − | − | − | − | − | − | − |
| 21.6.96 | ± | − | − | − | − | − | − | − | − |
| 26.6.96 | ± | − | − | − | − | − | − | − | − |
| 19.7.96 | ± | ± | − | − | − | − | − | ± | − |

TABLE 3-continued

VIRAL LOAD, LYMPHOCYTE AND SEROCONVERSION ANALYSES FOR PATIENT BM

| | | | | | | | | | |
|---|---|---|---|---|---|---|---|---|---|
| 1.10.96 | ± | ± | − | − | ± | − | − | ± | − |
| 8.11.96 | ± | ± | ± | − | − | − | − | ± | ± |

TABLE 4

VIRAL LOAD AND LYMPHOCYTE ANALYSES OF PATIENT TD

Infected November 1995,  
seroconverted Dec 1995  
Naive (never treated before)  
Hepatitis, March 1996

Therapy begun 29 July 96  
HU 300 mg TID  
ddI 200 mg BID  
INDINAVIR 800 mg TID

| VIRAL LOAD IN THE BLOOD | | | VIRAL LOAD IN THE LYMPH NODE | | | | VIRAL LOAD SEMEN | |
|---|---|---|---|---|---|---|---|---|
| D/M/Y | bDNA/PCR | PCR/RIGHT | M/D/Y p24 antigen expression | | HIV-RNA in situ | | HIV DNA PCR | D/M/Y |
| 08.03.96 | 47,940 | | FDC | Cells | FDC | Cells | | 07.01.97 |
| 13.03.96 | <10,000 | | 07.01.97 | | | | | <400 copies/ml |
| 25.04.96 | 39,290 | | − | − | − | − | negative | |
| 23.05.96 | 32,980 | | | | | | | |
| 20.06.96 | 30,090 | | | | | | | |
| 18.07.96 | 45,290 | | | | | | | |
| 22.07.96 | 42,000 | | | | | | | |
| 22.07.96 | 114,000 | | | | | | | |
| 01.08.96 | 48,000 | | | | | | | |
| 10.09.96 | 750 | | | | | | | |
| 21.10.96 | <500 | "neg?" | | | | | | |
| 04.11.96 | <500 | <200 | | | | | | |
| 23.12.96 | <500 | <200 | | | | | | |
| 30.1.97 | <400 | <200 | | | | | | |

LYMPHOCYTE POPULATION ANALYSIS

| D/M/Y | Lymph. | B.Ly | T-Ly | CD4 | CD4 % | CD8 | CD8 % | Ratio |
|---|---|---|---|---|---|---|---|---|
| 25.04.96 | 1745 | 90 | 1140 | 490 | 28 | 1010 | 58 | 0.49 |
| 23.05.96 | 1934 | 120 | 1620 | 620 | 32 | 1120 | 58 | 0.55 |
| 20.06.96 | 1885 | 110 | 1550 | 550 | 29 | 1060 | 56 | 0.52 |
| 18.07.96 | 1649 | 120 | 1340 | 480 | 29 | 970 | 59 | 0.49 |
| 10.09.96 | 2253 | 203 | 1794 | 879 | 39 | 1104 | 49 | 0.80 |
| 23.12.96 | 1560 | 156 | 1213 | 530 | 34 | 640 | 41 | 0.83 |
| 08.01.96 | 2504 | 225 | 2098 | 1102 | 44 | 1102 | 44 | 1.00 |
| 30.01.97 | 2448 | 269 | 1928 | 881 | 36 | 979 | 40 | 0.90 |
| 14.02.97 | 2545 | 204 | 2138 | 1069 | 42 | 1044 | 41 | 1.02 |

TABLE 5

VIRAL LOAD AND LYMPHOCYTE ANALYSES OF PATIENT LF

Infected May 95?  
Naive (never treated before)

Therapy begun 26 June 96  
HU 300 mg TID  
ddI 200 mg BID  
INDINAVIR 800 mg TID

| VIRAL LOAD IN THE BLOOD | | | VIRAL LOAD IN LYMPH NODE | | | | VIRAL LOAD | |
|---|---|---|---|---|---|---|---|---|
| D/M/Y | bDNA/PCR | PCR/RIGHT | D/M/Y p24 antigen expression | | HIV-RNA in situ | | HIV DNA PCR | SEMEN |
| 05.03.96 | 70,200 | | FDC | Cells | FDC | Cells | | 07.01.97 |
| 15.03.96 | 40,950 | | 07.01.97 | | | | | <400 copies/ml |
| 04.04.96 | 14,910 | | − | − | − | − | positive | |
| 10.5.96 | 27,290 | | | | | | | |
| 07.06.96 | 30,820 | | | | | | | |
| 12.07.96 | <500 | | | | | | | |
| 20.08.96 | <500 | | | | | | | |
| 24.09.96 | <500 | | | | | | | |
| 10.10.96 | <500 | | | | | | | |

TABLE 5-continued

VIRAL LOAD AND LYMPHOCYTE ANALYSES OF PATIENT LF

| | | |
|---|---|---|
| 08.11.96 | <400 | |
| 14.12.96 | <500 | |
| 7.1.97 | | <200 |

LYMPHOCYTE POPULATION ANALYSIS

| D/M/Y | Lymph. | B.Ly | T-Ly | CD4 | CD4 % | CD8 | CD8 % | Ratio |
|---|---|---|---|---|---|---|---|---|
| 06.03.96 | 2880 | 194 | 2095 | 693 | 25 | 1358 | 49 | 0.51 |
| 22.03.96 | 2772 | 168 | 2193 | 729 | 26 | 1374 | 49 | 0.53 |
| 10.05.96 | 3578 | 250 | 2650 | 790 | 22 | 1860 | 52 | 0.42 |
| 07.06.96 | 2756 | 190 | 1930 | 630 | 23 | 1490 | 54 | 0.42 |
| 12.07.96 | 2584 | 260 | 1880 | 750 | 29 | 1190 | 46 | 0.63 |
| 26.08.96 | 2268 | 249 | 1701 | 771 | 34 | 998 | 44 | 0.77 |
| 10.10.96 | 2508 | 201 | 1826 | 853 | 34 | 953 | 38 | 0.90 |
| 04.12.96 | 1888 | 189 | 1385 | 642 | 34 | 680 | 36 | 0.94 |
| 07.01.97 | 2350 | 235 | 1833 | 940 | 40 | 870 | 37 | 1.08 |

TABLE 6

VIRAL LOAD AND LYMPHOCYTE ANALYSES FOR PATIENT LJ

| | Therapy begun 28 March 96 | | Therapy changed 1 July 96 | |
|---|---|---|---|---|
| Infected 1987 or 1991 | HU | 300 mg TID | HU | 300 mg TID |
| | ddI | 200 mg BID | ddI | 200 mg BID |
| Naive (never treated before) | RITONAVIR | 600 mg BID | INDINAVIR | 800 mg TID |

VIRAL LOAD IN THE LYMPH NODE

| VIRAL LOAD IN THE BLOOD | | D/M/Y 2.10.96 | size: 6.5 × 12.5 | | 2 weeks a. neg | | VIRAL LOAD |
|---|---|---|---|---|---|---|---|
| D/M/Y | PCR/RIGHT | p24 antigen expression | | HIV-RNA in situ | | SEMEN | |
| 21.2.96 | | FDC | Cells | FDC | Cells | 07.01.97 | |
| 25.3.96 | 95229 | + | − | − | (few) + | <400 copies/ml | |
| 1.4.96 | | | | | | | |
| 23.4.96 | 757 | | | | | | |
| 7.5.96 | | | | | | | |
| 30.5.96 | 836 | | | | | | |
| 28.6.96 | 393 | | | | | | |
| 22.7.96 | 347 | | | | | | |
| 6.8.96 | | | | | | | |
| 5.9.96 | | | | | | | |
| 19.9.96 | <200 | | | | | | |
| 14.10.96 | <200 | | | | | | |
| 18.11.96 | | | | | | | |
| 4.12.96 | <200 | | | | | | |
| 18.12.96 | | | | | | | |
| 28.1.97 | <200 | | | | | | |

LYMPHOCYTE POPULATION ANALYSIS

| D/M/Y | Lymph. | B.Ly | T-Ly | CD4 | CD4 % | CD8 | CD8 % | Ratio |
|---|---|---|---|---|---|---|---|---|
| 09.02.96 | 1,680 | 176 | 1,382 | 303 | 19 | 1,053 | 66 | 0.29 |
| 22.02.96 | 2,178 | 220 | 1,960 | 374 | 17 | 1,560 | 71 | 0.24 |
| 26.03.96 | 1,754 | 190 | 1,490 | 330 | 19 | 1,190 | 68 | 0.28 |
| 01.04.96 | 2,317 | 260 | 2,020 | 420 | 18 | 1,600 | 69 | 0.26 |
| 08.05.96 | 1,946 | 230 | 1,640 | 330 | 17 | 1,380 | 71 | 0.24 |
| 30.05.96 | 2,346 | 230 | 1,970 | 400 | 17 | 1,710 | 73 | 0.23 |
| 22.07.96 | 1,544 | 220 | 1,310 | 340 | 22 | 990 | 64 | 0.34 |
| 23.08.96 | 1,640 | 200 | 1,390 | 360 | 22 | 1,020 | 62 | 0.35 |
| 14.10.96 | 1,830 | 220 | 1,537 | 439 | 24 | 1,061 | 58 | 0.41 |
| 04.12.96 | 1,447 | 130 | 1,270 | 362 | 25 | 897 | 62 | 0.40 |
| 17.01.97 | 1,685 | 185 | 1,445 | 438 | 26 | 1,078 | 64 | 0.41 |
| 28.01.97 | 1,260 | 126 | 1,098 | 290 | 23 | 794 | 63 | 0.37 |

We claim:

1. A method for inhibiting the replication of the human retrovirus selected from the group consisting of HIV-1, HIV-2, HTLV-1, and HTLV-2 comprising the step of co-administering to human cells dideoxyinosine, hydroxyurea, and at least one HIV protease inhibitor.

2. The method of claim 1, wherein said cells are in vivo.

3. The method of claim 1 wherein said virus is a human retrovirus selected from the group consisting of HIV-1, HIV-2, HTLV-1 and HTLV-II and said cells are human cells.

4. The method of claim 1 wherein said protease inhibitor is selected from hydroxyethylamine derivatives, hydroxyethylene derivatives, (hydroxyethyl)urea derivatives, norastine derivatives, symmetric dihydroxyethylene derivatives, derivatives containing the dihydroxyethylene transition state isostere, penicillin-derived compounds, non-peptide cyclic ureas, and mixtures thereof.

5. The method of claim 1 wherein said combination of compounds is administered to a human being before acute viral infection.

6. The method of claim 1 wherein said combination of compounds is administered to a human being before seroconversion.

7. The method of claim 1 wherein said combination of compounds is administered to a human being after seroconversion.

\* \* \* \* \*